(12) United States Patent
Keren

(10) Patent No.: US 6,807,443 B2
(45) Date of Patent: Oct. 19, 2004

(54) HIGH-RESOLUTION MEDICAL MONITORING APPARATUS PARTICULARLY USEFUL FOR ELECTROCARDIOGRAPHS

(75) Inventor: Hanan Keren, Kfar Saba (IL)

(73) Assignee: Cheetah Medical Inc., Wilmington, DE (US)

( * ) Notice: Subject to any disclaimer, the term of this patent is extended or adjusted under 35 U.S.C. 154(b) by 351 days.

(21) Appl. No.: 10/134,380

(22) Filed: Apr. 30, 2002

(65) Prior Publication Data

US 2002/0198460 A1 Dec. 26, 2002

Related U.S. Application Data (60) Provisional application No. 60/287,778, filed on May 1, 2001.

(51) Int. Cl.[7] .............................................. A61B 5/04
(52) U.S. Cl. ................................................... 600/509
(58) Field of Search ................................ 600/509, 534, 600/536; 607/28, 29; 128/901, 902

(56) References Cited

U.S. PATENT DOCUMENTS

| | | | | |
|---|---|---|---|---|
| 4,506,678 A | * | 3/1985 | Russell et al. | 600/536 |
| 4,628,939 A | * | 12/1986 | Little et al. | 600/509 |
| 5,330,512 A | * | 7/1994 | Hauck et al. | 607/28 |

* cited by examiner

Primary Examiner—George Manuel
(74) Attorney, Agent, or Firm—G. E. Ehrlich (1995) Ltd.

(57) ABSTRACT

Medical monitoring apparatus to be used in an environment including electrical supply lines of a particular line frequency, for monitoring a particular body activity and for producing an electrical output signal corresponding to the monitored body activity includes: a first filter network connected to receive the electrical output signal and tuned to the line frequency for rejecting the line frequency component of the electrical output signal; a second filter network connected to receive the output of the first filter network and also tuned to the line frequency for rejecting the line frequency component of the electrical output signal; and a high impedance coupling between the first and second filter networks.

8 Claims, 11 Drawing Sheets

HIGH-RESOLUTION MEDICAL MONITORING APPARATUS PARTICULARLY USEFUL FOR ELECTROCARDIOGRAPHS

This application claims the benefit of Provisional application No. 60/287,778 filed May 1, 2001.

FIELD AND BACKGROUND OF THE INVENTION

The present invention relates to high resolution medical monitoring apparatus. The invention is particularly useful in electrocardiograph (ECG) apparatus for monitoring ECG signals accompanying heart activity, and the invention is therefore described below particularly with respect to this application.

In ECG apparatus, a plurality of electrodes placed on the patient detect electrical signals accompanying heart activity and feed these signals through a multi-conductor cable to the ECG recorder. The ECG apparatus is usually used in environments where electrical noise from adjacent power lines is inductively coupled to the ECG cable, thereby adding a significant amount of electrical noise induced from the electrical supply lines to the ECG signals which are relatively weak. Accordingly, the S/N (signal-to-noise) ratio of the ECG signal can be fairly low. Moreover, the 50 Hz or 60 Hz frequency of the electrical supply line noise is within the frequency spectrum of the ECG signals.

Various types of filters have been devised for increasing the S/N ratio in medical monitoring equipment in general, and in ECG apparatus in particular, but efforts are continuously being made to devise new filter networks to increase the S/N ratio because of the importance of the ECG signal in providing information on the condition and performance of the heart.

BRIEF SUMMARY OF THE PRESENT INVENTION

According to one aspect of the present invention, there is provided medical monitoring apparatus to be used in an environment of electrical supply lines of a particular line frequency, for monitoring a particular body activity and for producing an electrical output signal corresponding to the monitored body activity; the apparatus, comprising: a first filter network connected to receive the electrical output signal and tuned to the supply line frequency for rejecting the line frequency component of the electrical output signal; a second filter network connected to receive the output of the first filter network and also tuned to the line frequency for rejecting the line frequency component of the electrical output signal; and a high impedance coupling between the first and second filter networks.

According to further features in the preferred embodiments of the invention described below, at least one of the filter networks, and preferably both, include a first capacitor and a second capacitor connected in series with each other to ground; and an operational amplifier having one input connected from a point between the second capacitor and ground, an output connected to a point between the first and second capacitors, and a second input connect to the output of the operational amplifier.

In one described preferred embodiment, the high impedance coupling between the first and second filter networks is an electrical resistor network; and in a second described preferred embodiment, the high impedance coupling between the first and second filter networks is a buffer amplifier.

According to another aspect of the present invention, there is provided medical monitoring apparatus to be used in an environment of electrical supply lines of a particular line frequency, for monitoring a particular body activity and for producing an electrical output signal corresponding to the monitored body activity; the apparatus, including a filter network connected to receive the electrical output signal and tuned to the supply line frequency for rejecting the line frequency component of the electrical output signal, the filter network comprising a first capacitor and a second capacitor connected in series with each other to ground; and an operational amplifier having one input connected from a point between the second capacitor and ground, an output connected to a point between the first and second capacitors, and a second input connect to the output of the operational amplifier.

As will be described more particularly below, particularly good results are obtainable when the medical monitoring apparatus monitors electrocardiograph (ECG) signals accompanying heart activity.

Further features and advantages of the invention will be apparent from the description below.

BRIEF DESCRIPTION OF THE DRAWINGS

The invention is herein described, by way of example only, with reference to the accompanying drawings, wherein.

BASIC ECG WAVEFORMS

Figure 1:
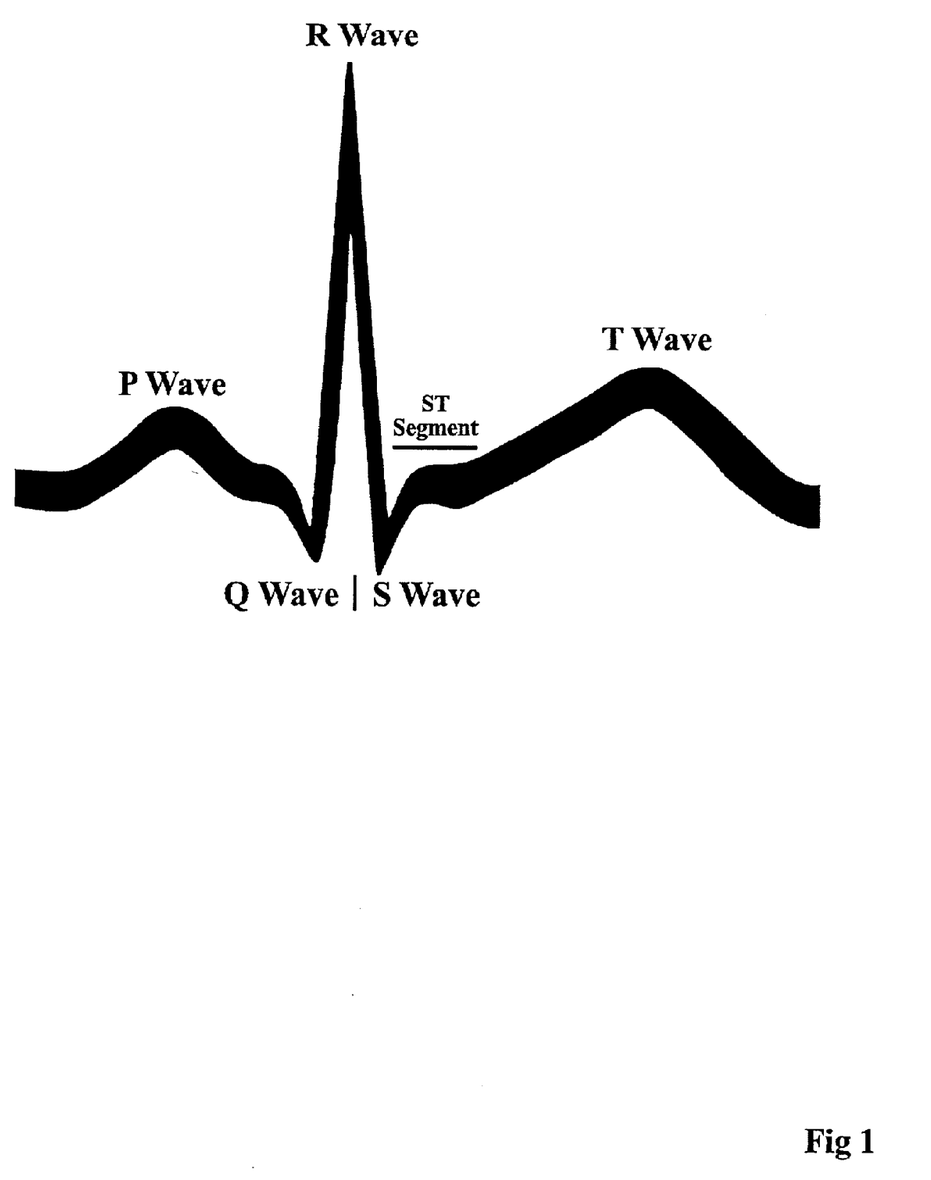
FIG. 1 illustrates a basic ECG waveform.

The ECG is the graphic record of the electrical activity of the human heart obtained by applying three electrodes to the left hand, right hand and foot of the patient, and six chest electrodes applied to various locations on the patients chest. FIG. 1 illustrates the basic ECG tracing of a subject having a normal-functioning heart.

As can be seen from FIG. 1, the ECG tracing comprises a series of waveforms shown at P, Q, R, ST and T in FIG. 1.

The first little upward notch of the ECG tracing is called the "P wave". The P wave indicates that the atria (the two upper chambers of the heart) are contracting to pump out blood.

The next part of the tracing is a short downward section connected to a tall upward section. This next part is called the "QRS complex". This part indicates that the ventricles (the two lower chambers of the heart) are contracting to pump out blood.

The next short upward segment is called the "ST segment". The ST segment indicates the amount of time from the end of the contraction of the ventricles to the beginning of the rest period before the ventricles begin to contract for the next beat.

The next upward curve is called the "T wave". The T wave indicates the resting period of the ventricles.

As indicated earlier, an accurate diagnosis of the condition and operation of the patient's heart requires removable, to the highest degree possible, the noise in the produced ECG signal, particularly the 50-cycle (or 60-cycle) line frequency noise induced from electrical supply lines in the area of the apparatus, in order to increase the S/N ratio to the highest degree possible.

DESCRIPTION OF PREFERRED EMBODIMENTS

Figure 2:
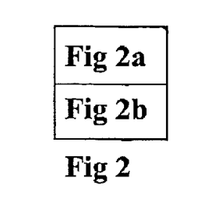
FIG. 2 is an electrical diagram of the first amplifier stage in ECG apparatus constructed in accordance with the present invention.
Figure 2A:
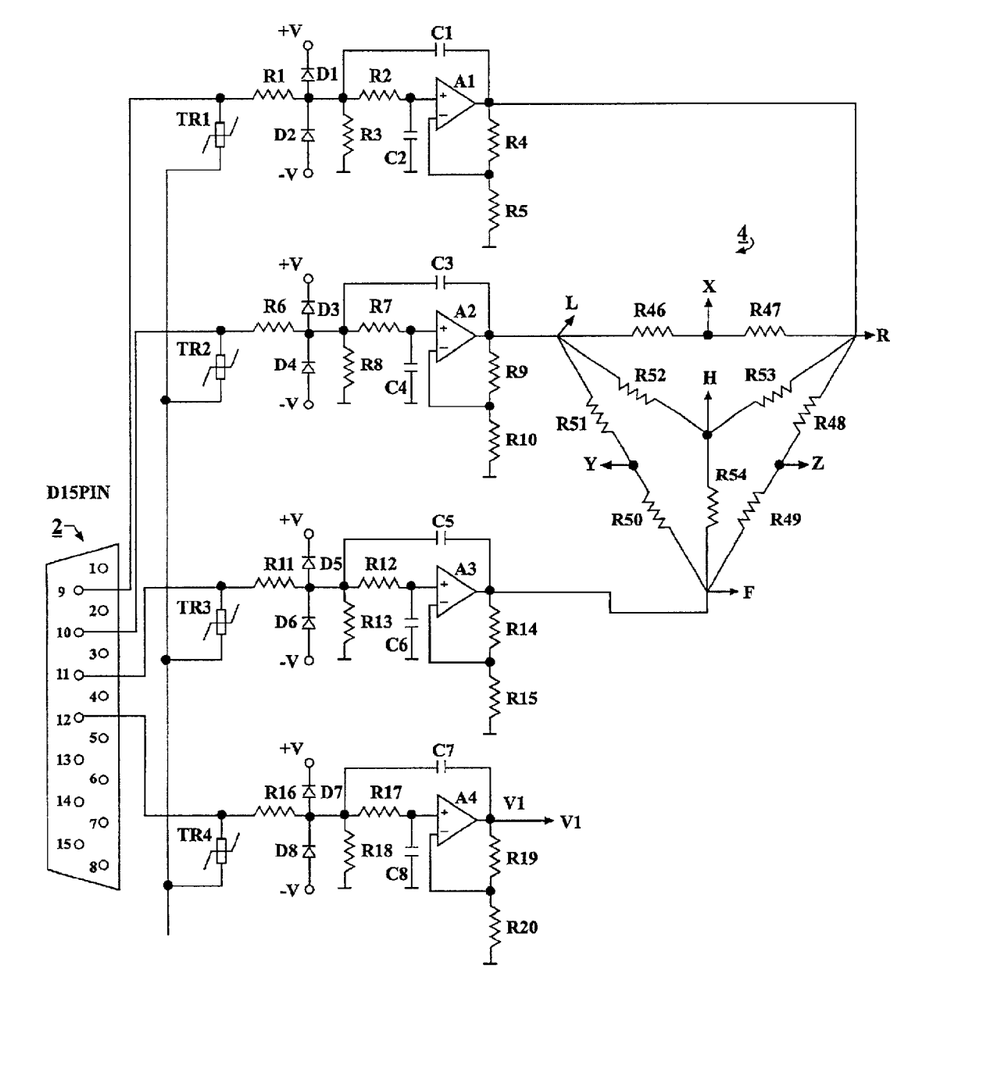
Figure 2B:
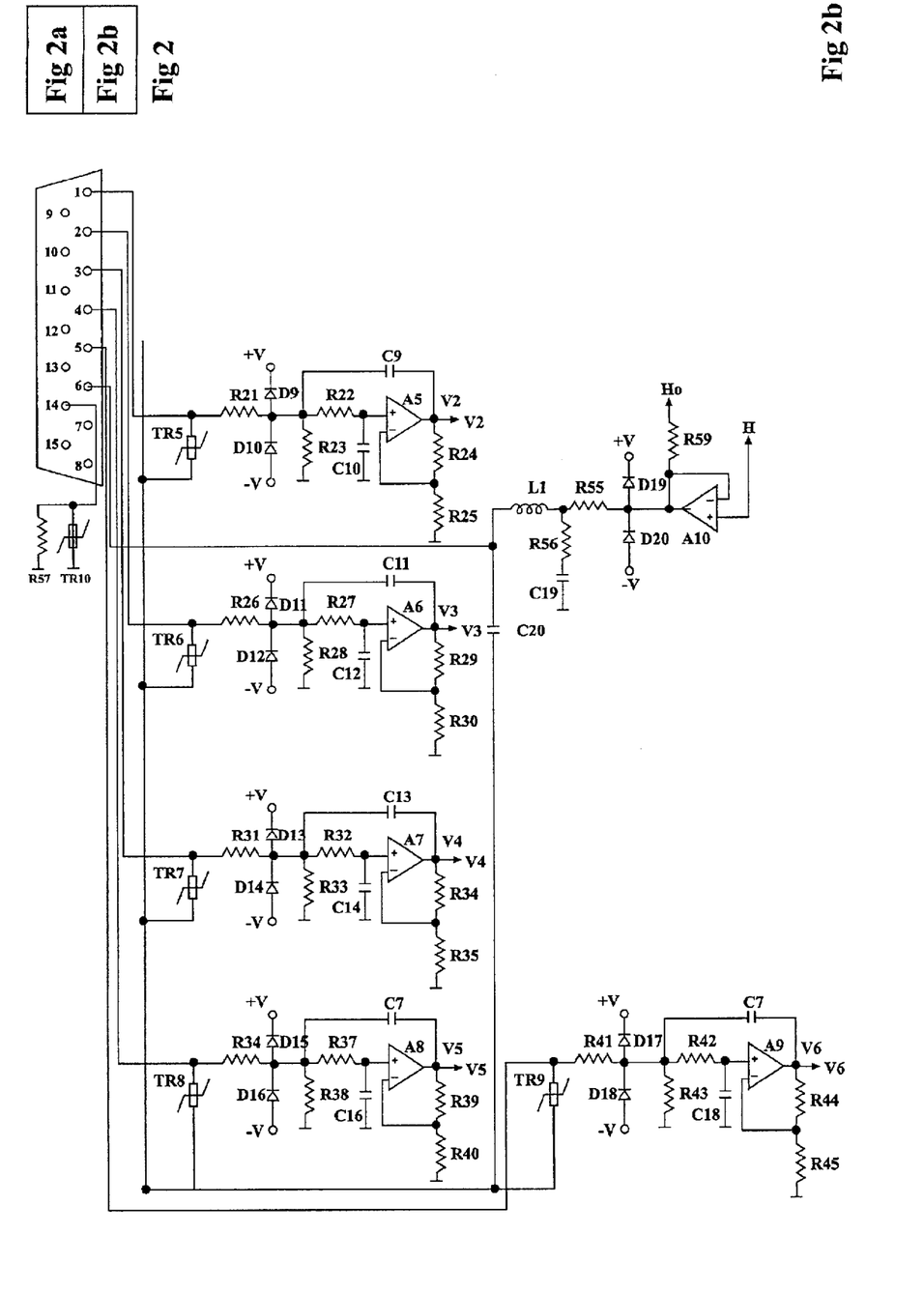
Figures 3, 3A:
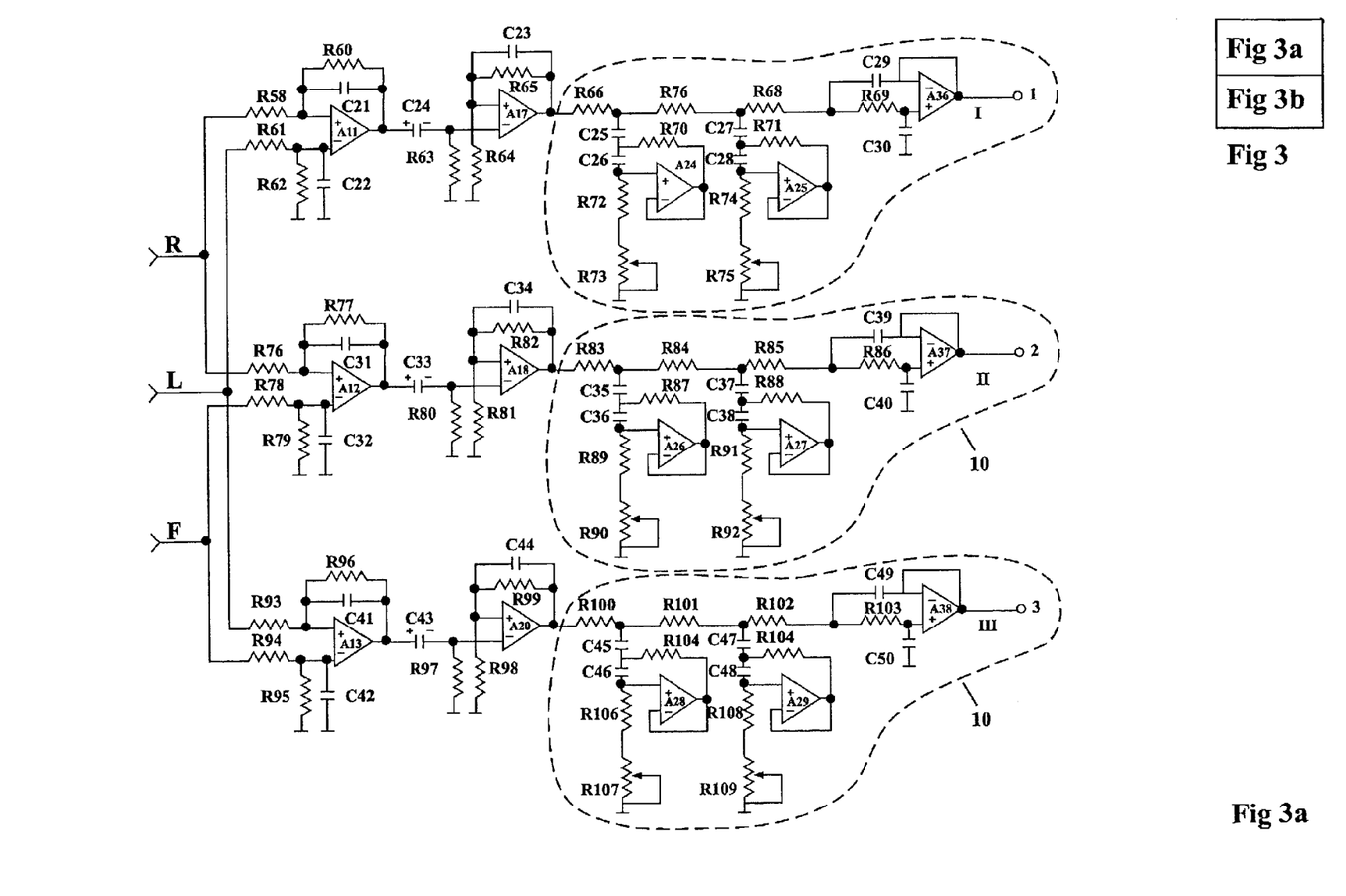
FIG. 3 is an electrical diagram of the second amplifier stage in ECG apparatus constructed in accordance with the present invention for amplifying the outputs of the three existing electrodes (two hand electrodes and foot electrode) applied to the patient.
Figure 3B:
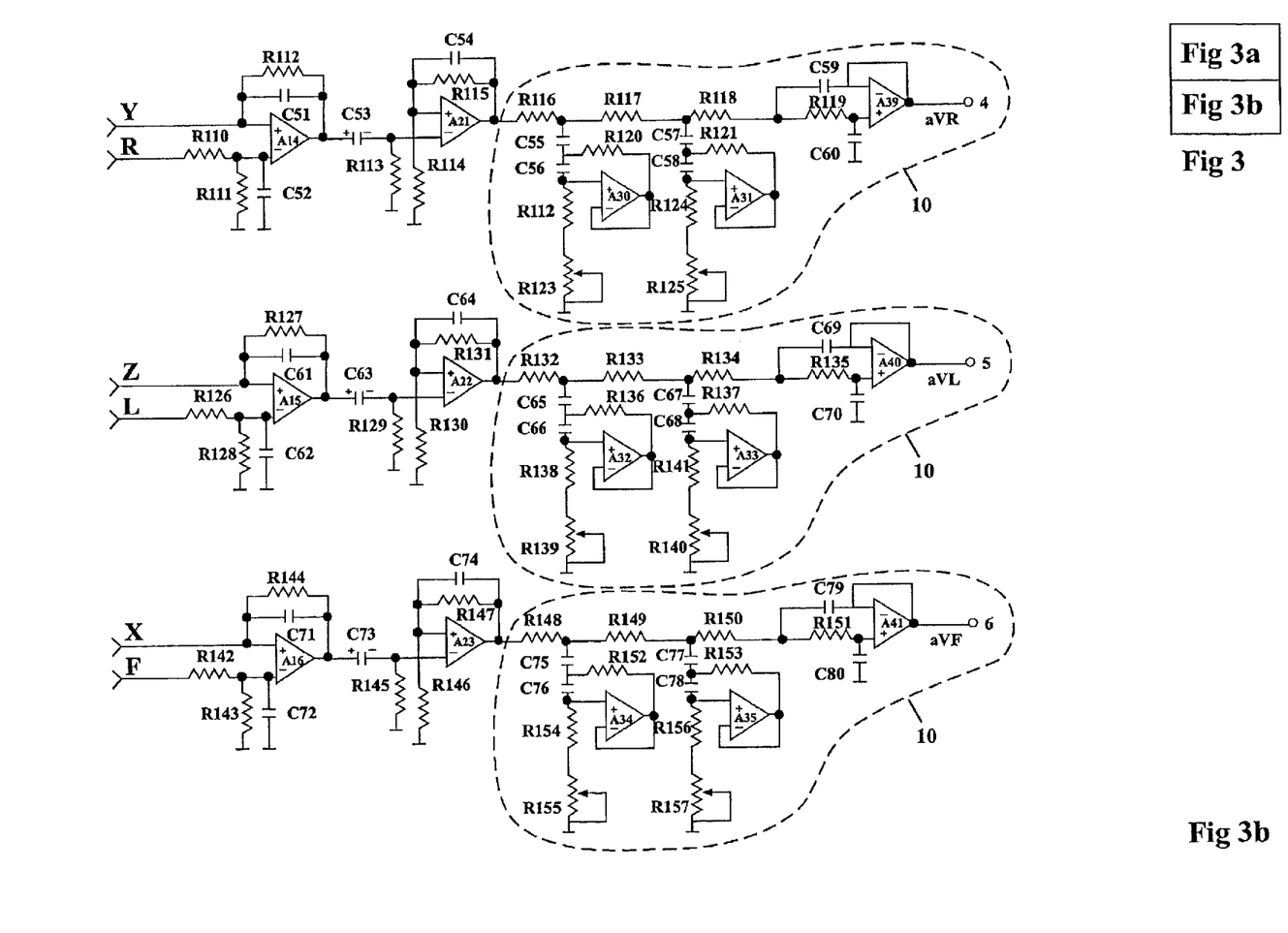
Figures 4, 4A:
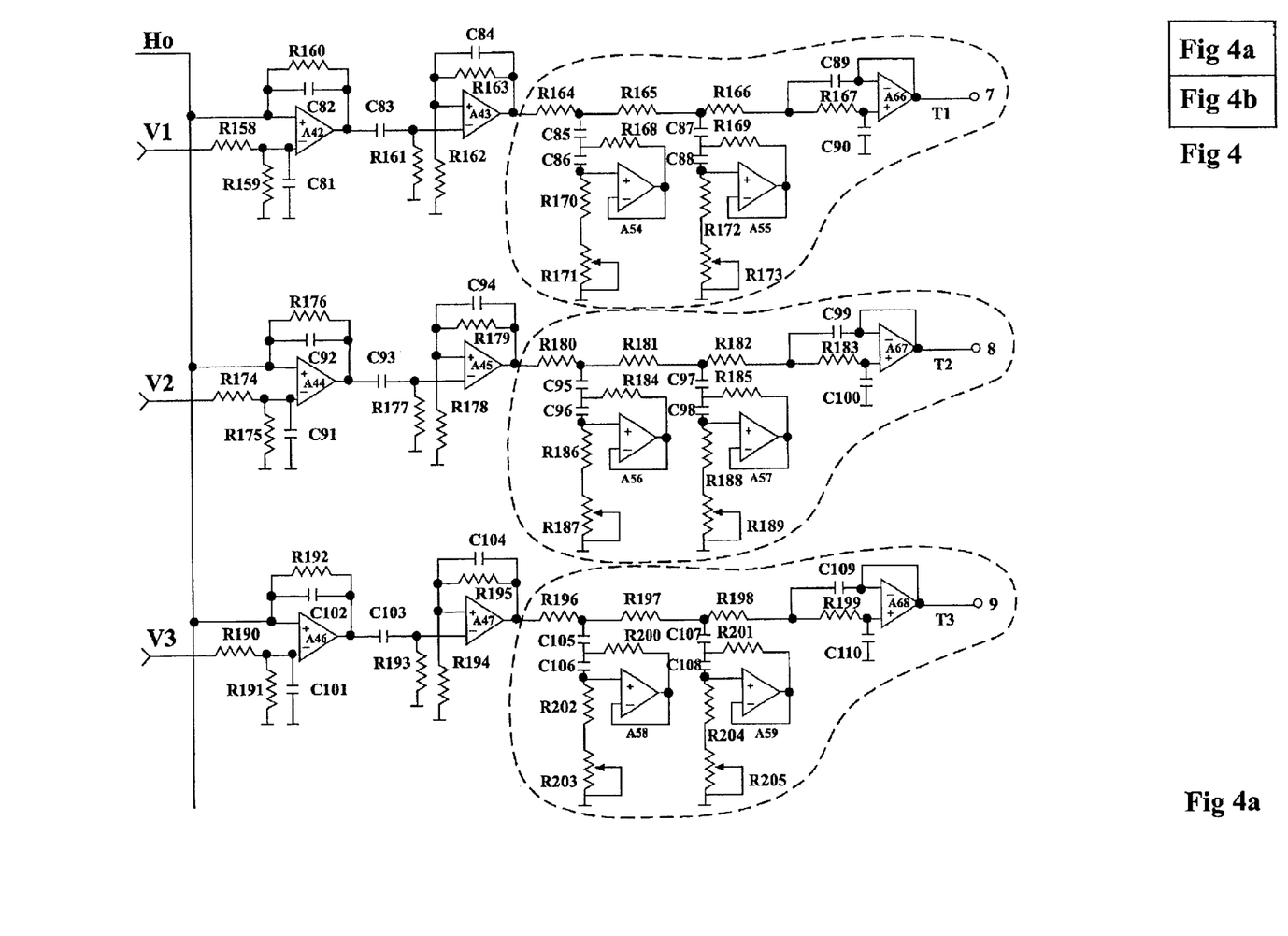
FIG. 4 is an electrical diagram illustrating the second amplifier stage for amplifying the outputs of the six chest electrodes applied to the patient.
Figure 4B:
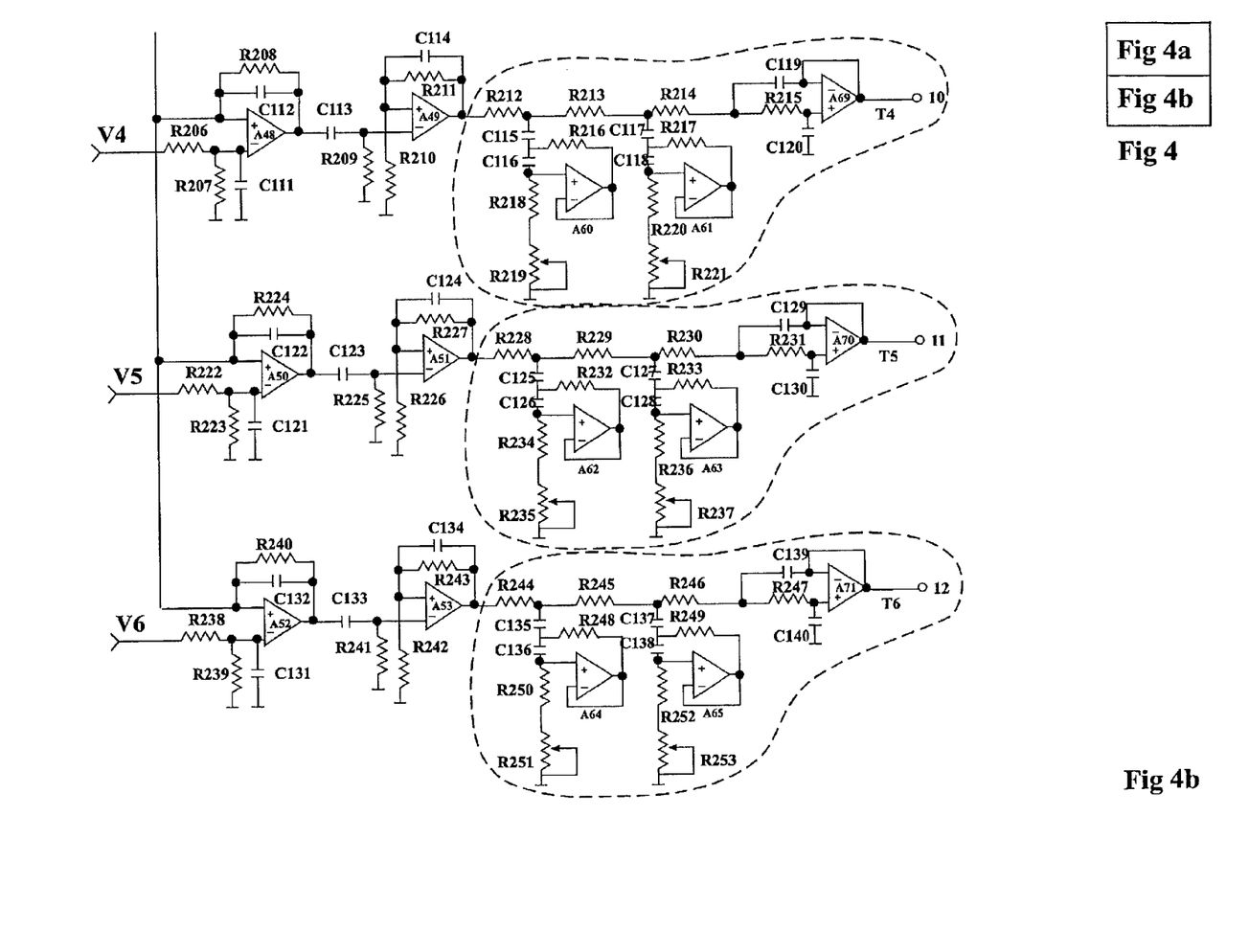
Figure 5:
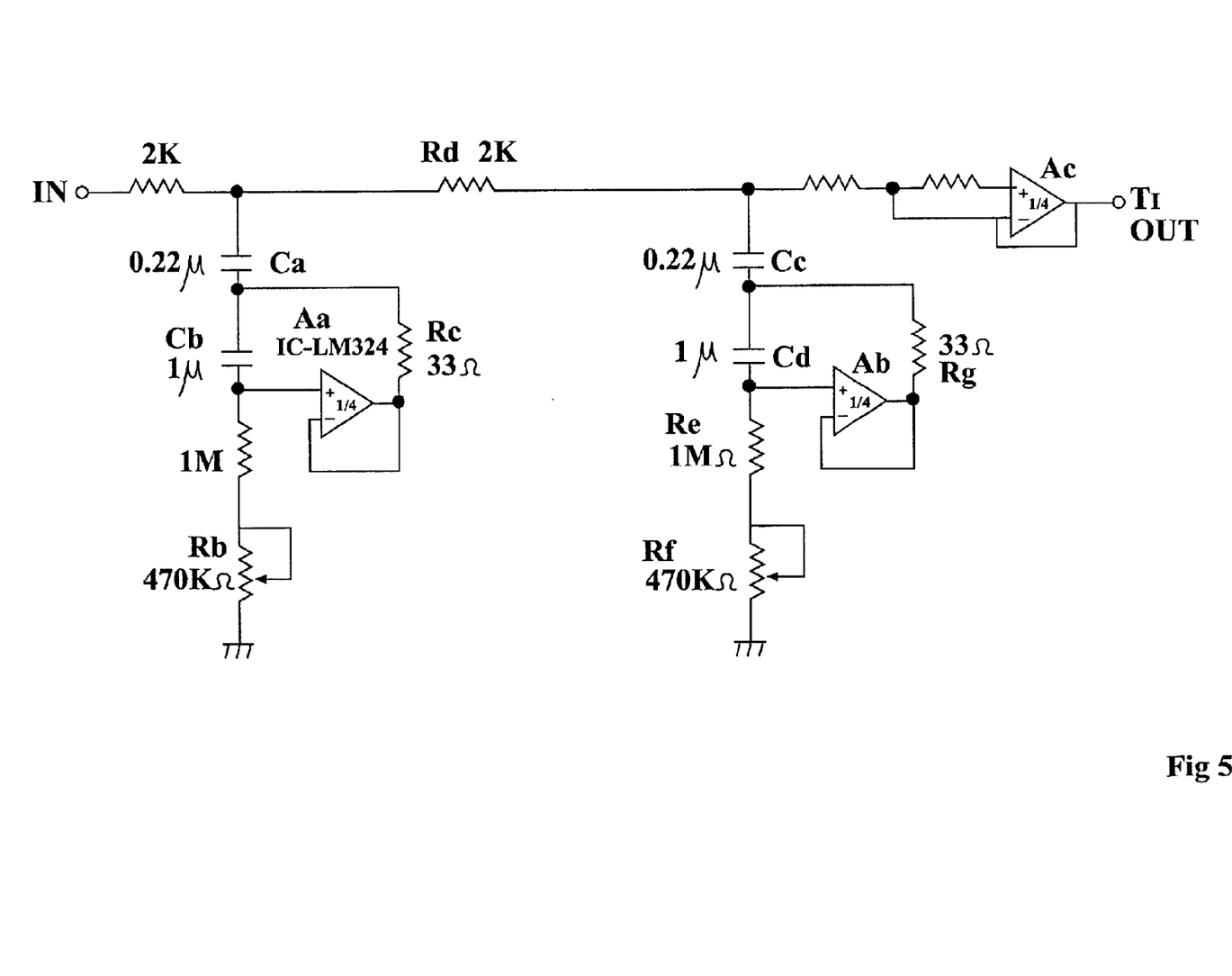
FIG. 5 is an electrical diagram more particularly illustrating the construction of the notch filter in each of the ECG signal channels illustrated in FIGS. 3 and 4.
Figure 6:
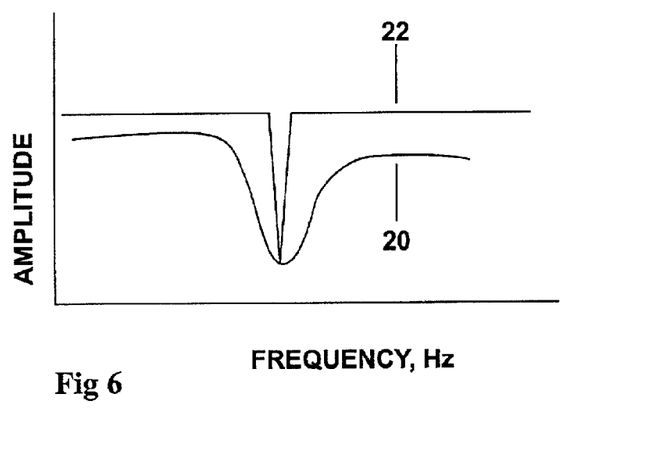
FIG. 6 diagrammatically illustrates the improvement in the operation of the notch filter shown in FIGS. 3–6, as compared to a standard notch filter.
Figure 7:
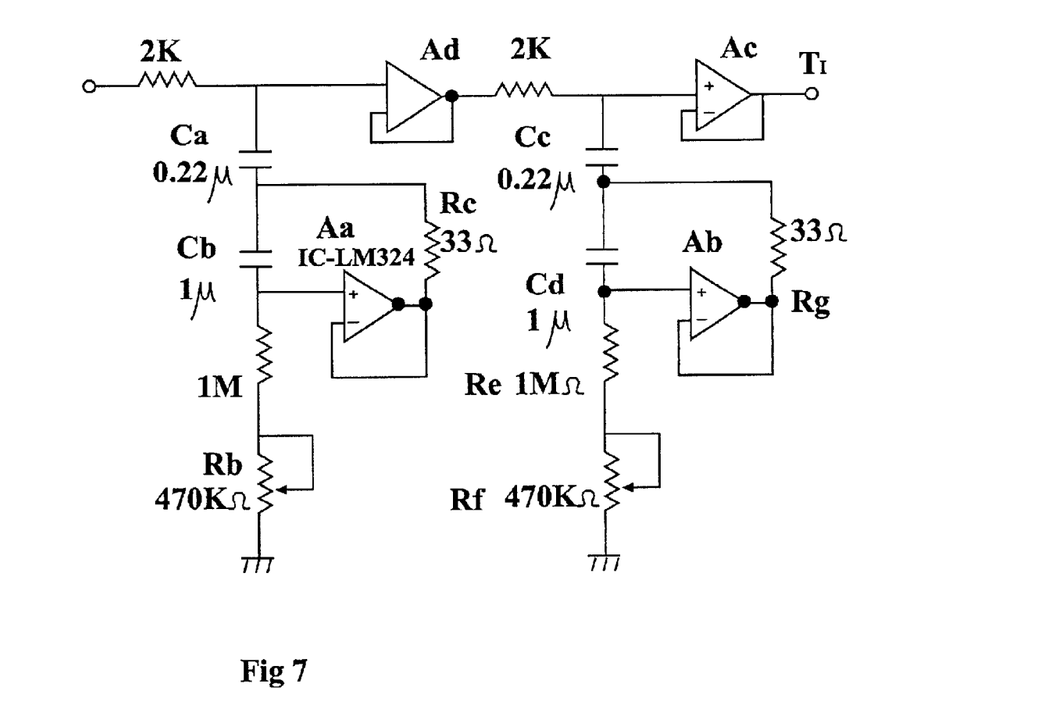
FIG. 7 illustrates a modification in the notch filter of FIG. 5.
Figure 8:
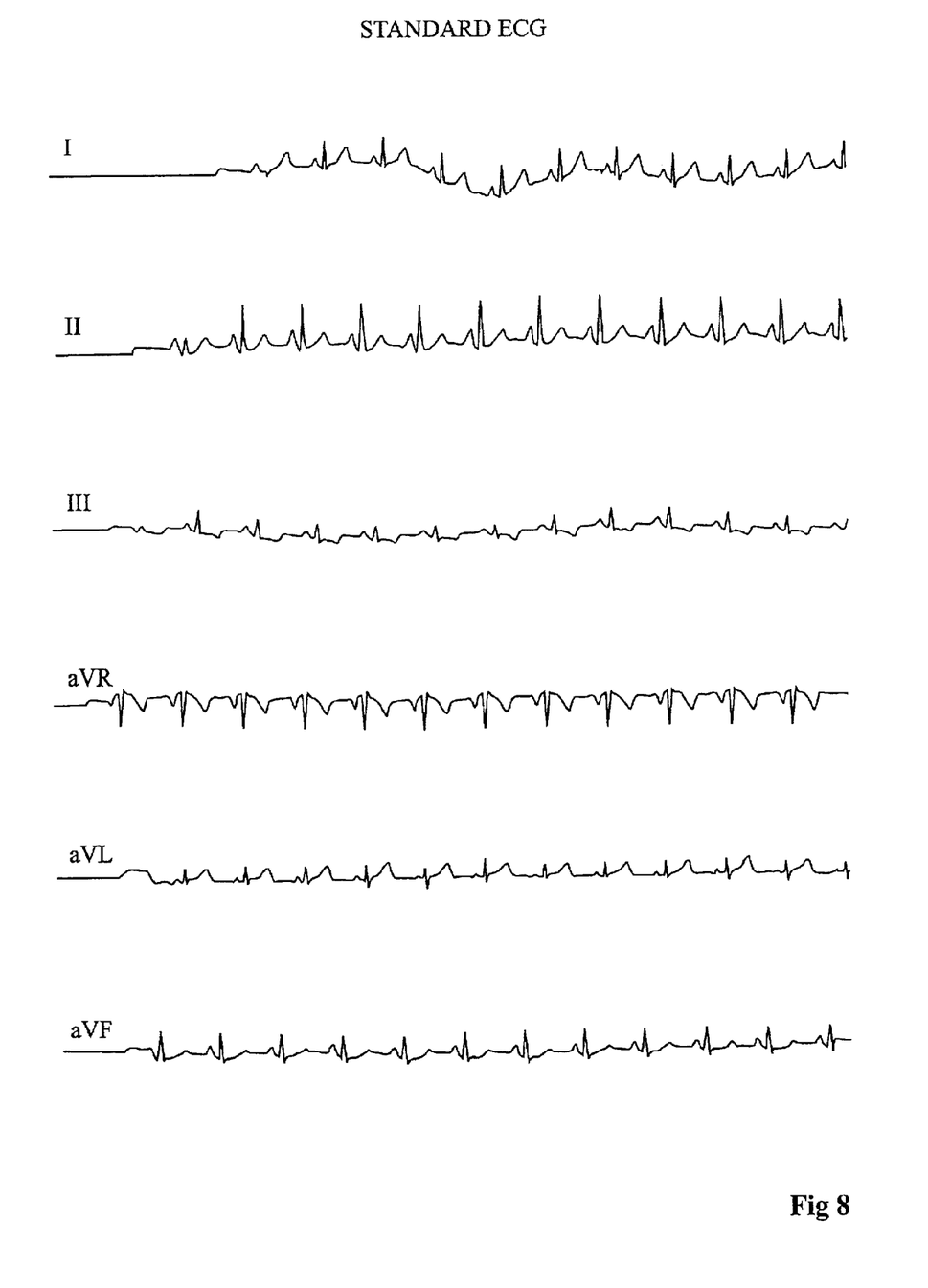
FIG. 8 illustrates ECG recordings when made with conventional ECG apparatus.
Figure 9:
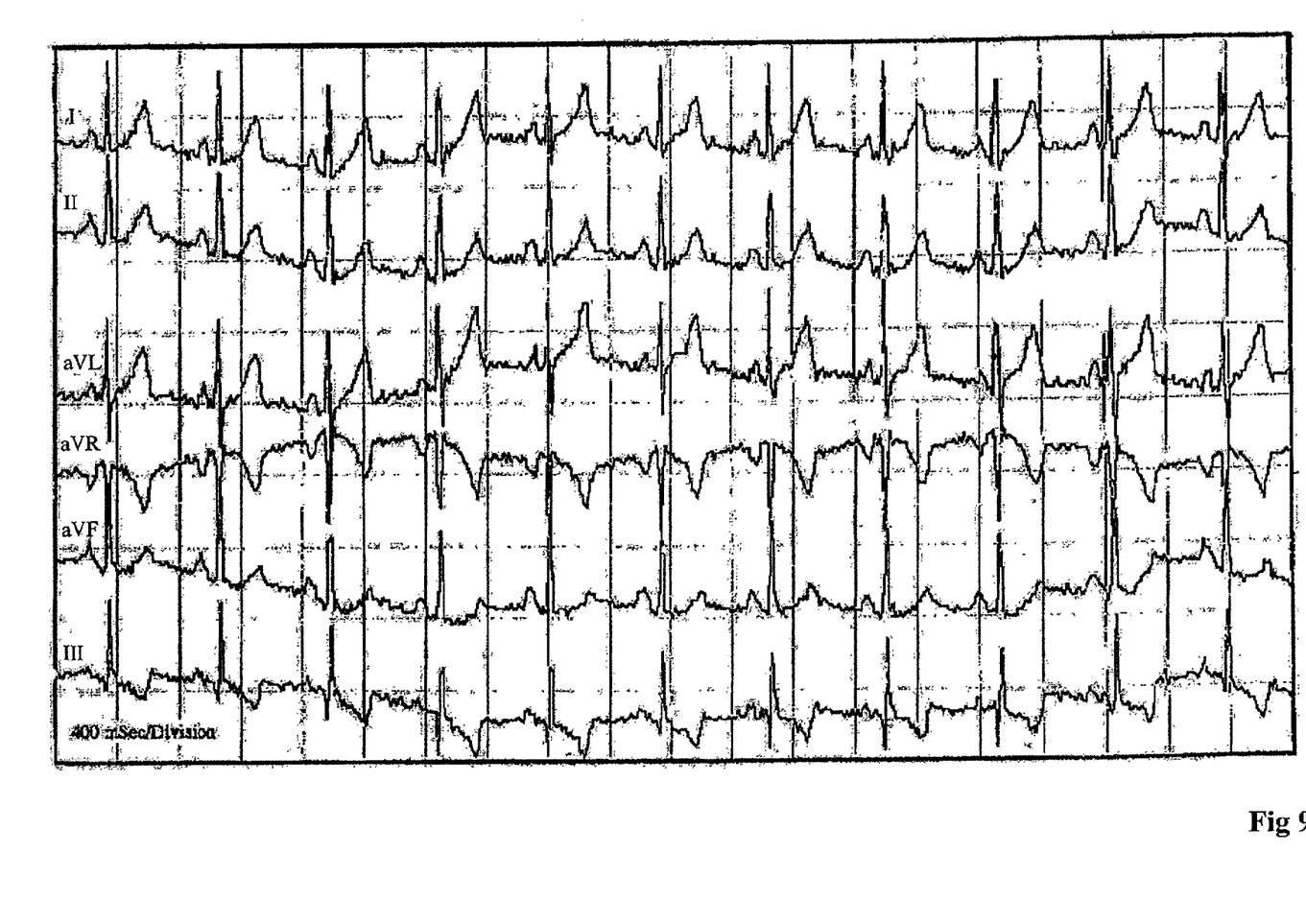
FIG. 9 illustrates ECG recordings when made utilizing the apparatus of the present invention as described herein.

FIGS. 2–4 illustrate one form of ECG apparatus constructed in accordance with the present invention and including a sharp notch filter for removing the line-frequency components of the noise from the ECG signal; FIG. 5 more particularly illustrates the construction of the notch filter in the portion of the apparatus illustrated in FIGS. 3 and 4; FIG. 6 illustrates the sharp frequency-rejection characteristics in the novel notch filter; FIG. 7 illustrates a modification in the construction of the notch filter; FIG. 8 illustrates typical ECG signals produced with conventional ECG apparatus; and FIG. 9 illustrates typical ECG signals produced with apparatus including notch filters constructed in accordance with the present invention, FIG. 2 illustrates the first amplifier stage of the ECG apparatus. This portion of the apparatus is basically similar to the first amplifier stage in conventional ECG apparatus. Thus, it includes a conventional 15-pin connector, generally designated 2, connected to the left and right (L, R) hand electrodes; the foot (F) electrode; the six chest electrodes ($V_1$–$V_6$); and the ground. The L, R and F electrodes are connected to the conventional Einthoven Triangle bridge circuit, generally designated 4, via amplifiers $A_1$, $A_2$, $A_3$, respectively; whereas the six chest electrodes $V_1$–$V_6$ are connected to points $V_1$–$V_6$, respectively, via amplifiers $A_4$–$A_9$. FIG. 2 also illustrates the reference voltage H applied via amplifier $A_{10}$ to produce the reference voltage HO.

Since the first amplifier stage as illustrated in FIG. 2 is basically similar to that included in the conventional ECG apparatus, further details of the circuitry are not described herein.

FIG. 3 illustrate the amplifier stage for amplifying the signals at points R, L, F, of bridge 4, to produce the outputs I, II, III. FIG. 3 further illustrates the amplifiers for amplifying the signals at points Y, R, to produce the output at TaVR; the signals at point Z, L, to produce the output at TaVL; and the signals at points X, F, to produce the outputs at TaVF. These amplifier stages include operational amplifiers $A_{11}$–$A_{16}$, and buffer amplifiers $A_{17}$–$A_{23}$ having high input impedances to permit extracting the respective ECG signal without loading the previous stage.

In accordance with the present invention, each of the ECG channels I, II, III, aVR, aVL, aVF includes a notch filter, generally designated 10, constructed in accordance with the present invention, tuned to the supply line frequency (e.g., 50 Hz or 60 Hz) for rejecting the line frequency noise component in the respective ECG signal, to thereby increase the S/N ratio. The construction of each of the notch filters 10 is more particularly illustrated in FIG. 5.

As shown in FIG. 5, each notch filter 10 is of a two-stage construction, including two filter networks connected together with a high impedance coupling between them. Each stage is tuned to the supply line frequency for rejecting the line frequency component of the respective ECG signal by bypassing that component to the ground.

Whereas the conventional filter networks generally include a capacitance (C) and an inductance (L), which are tuned to the frequency to be rejected, the filter network illustrated in FIG. 5 avoids the use of a conventional inductor, and instead uses the combination of another capacitor and an operational amplifier to permit tuning the filter network. Such an arrangement permits a more compact construction than would be possible using a conventional inductor.

Thus, as shown in FIG. 5, the first stage filter network includes a first capacitor Ca and a second capacitor Cb connected in series with each other to ground, and an operational amplifier Aa. Operational amplifier Aa has a plus input from a point between the second capacitor Cb and ground; a minus input connected to its output; and an output connected via a resistor $R_c$ to a point between the two capacitors Ca, Cb. FIG. 5 illustrates typical values for tuning this filter network to reject the line frequency component of the ECG signal where the supply line frequency is 50 Hz.

The second filter network is similarly constructed with two capacitors Cc, Cd, and with an operational amplifier Ab. This filter network is coupled by resistor Rd to the first filter network and is also tuned to the supply line frequency for rejecting the line frequency component (50 Hz) in the ECG signal outputted from the first filter network. The output from the second filter network is fed via another buffer amplifier $A_c$ to the respective ECG signal terminal $T_I$ for recording.

FIG. 6 illustrates the reject characteristics of the notch filter as described above, as compared to a conventional notch filter. Thus, whereas in a conventional notch filter the reject frequency band is relatively wide, as shown by curve 20 in FIG. 6, using the notch filter as described above has been found to produce a very narrow frequency reject band, as shown at 22. Accordingly, such a filter is more effective to remove the line-frequency noise component (50 Hz, 60 Hz) from the ECG signal, while minimizing the removal of signal components in adjacent frequencies, thereby increasing the SNR ratio in the outputted signal.

Each of the other channels shown in FIG. 3 also includes a notch filter 10 of the foregoing construction, so that they also produce output signals at output terminals $T_I$, $T_{II}$, $T_{III}$, $T_{AVR}$, $T_{AVL}$, and $T_{AVF}$ having high SNR ratios.

Each of the recording channels shown in FIG. 4 is similarly constructed as shown in FIG. 3, including notch filters of the same construction as described above with respect to FIGS. 3, 5, and 6, such that the outputs of each channel as shown at terminals $T_1$ - - - $T_6$, will also have a high S/N ratio.

FIG. 7 illustrates a variation in the construction of the notch filter 10, wherein the high impedance coupling between the two filter stages is by a buffer amplifier Ad.

FIG. 8 illustrates a set of ECG signals produced with a standard ECG apparatus; whereas FIG. 9 illustrates a corresponding set of ECG signals produced by ECG apparatus equipped with the notch filters as described above. It will be seen that signals illustrated in FIG. 9 are significantly sharper than those illustrated in FIG. 8, and particularly better enable the discernment of the ratio of the R-wave to the T-wave; the F-wave; and the peak of the T-wave, all of which are important for determining the condition and operation of the heart of the patient being examined.

While the invention has been described with respect to one preferred embodiment, it will be appreciated that this is set forth merely for purposes of example, and that many other variations, modifications and applications of the invention may be made.

What is claimed is:

1. Medical monitoring apparatus to be used in an environment including electrical supply lines of a particular line frequency, for monitoring a particular body activity and for producing an electrical output signal corresponding to the monitored body activity; said apparatus, comprising:

a first filter network connected to receive said electrical output signal and tuned to said line frequency for rejecting the line frequency component of said electrical output signal;

a second filter network connected to receive the output of said first filter network and also tuned to said line frequency for rejecting the line frequency component of said electrical output signal;

and a high impedance coupling between said first and second filter networks.

2. The apparatus according to claim 1, wherein at least one of said filter networks includes:

a first capacitor and a second capacitor connected in series with each other to ground;

and an operational amplifier having one input connected from a point between the second capacitor and ground, an output connected to a point between the first and second capacitors, and a second input connect to said output of the operational amplifier.

3. The apparatus according to claim 2, wherein both of said filter networks include said first capacitor, said second capacitor, said operational amplifier, and the electrical connections therebetween.

4. The apparatus according to claim 1, wherein said high impedance coupling between the first and second filter networks is an electrical resistor network.

5. The apparatus according to claim 1, wherein said high impedance coupling between said first and second filter networks is a buffer amplifier.

6. The apparatus according to claim 1, wherein the monitoring apparatus monitors electrocardiograph signals accompanying heart activity.

7. Medical monitoring apparatus to be used in an environment of electrical supply lines of a particular line frequency, for monitoring a particular body activity and for producing an electrical output signal corresponding to the monitored body activity; said apparatus, including a filter network connected to receive said electrical output signal and tuned to said line frequency for rejecting the line frequency component of said electrical output signal; said filter network comprising:

a first capacitor and a second capacitor connected in series with each other to ground;

and an operational amplifier having one input connected from a point between the second capacitor and ground, an output connected to a point between the first and second capacitors, and a second input connect to said output of the operational amplifier.

8. The apparatus according to claim 7, wherein the monitoring apparatus monitor electrocardiograph signals accompanying heart activity.

* * * * *